Figure 1:
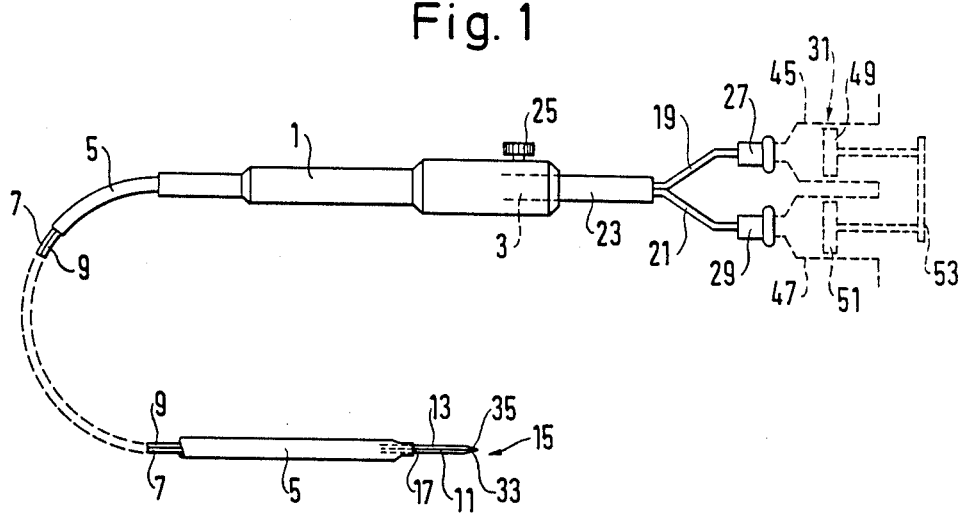

United States Patent [19]

Maslanka

[11] Patent Number: 4,932,942

[45] Date of Patent: Jun. 12, 1990

[54] INJECTION EQUIPMENT WITH A TWIN TUBULAR NEEDLE FOR AN ENDOSCOPE

[76] Inventor: Harald Maslanka, Stockacher Strasse 172, 7200 Tuttlingen, Fed. Rep. of Germany

[21] Appl. No.: 217,455

[22] Filed: Jul. 11, 1988

[30] Foreign Application Priority Data

Jul. 10, 1987 [DE] Fed. Rep. of Germany ....... 3722904

[51] Int. Cl.⁵ .................... A61M 25/00; A61M 5/00
[52] U.S. Cl. ..................... 604/164; 604/44; 604/83
[58] Field of Search ............. 128/4, 6; 604/43–45, 604/158–169, 83

[56] References Cited

U.S. PATENT DOCUMENTS

| | | | |
|---|---|---|---|
| 3,385,300 | 5/1968 | Holter | 604/43 X |
| 3,804,097 | 4/1974 | Rudie | 604/44 X |
| 4,134,402 | 1/1979 | Mahurkar | 604/44 |
| 4,222,380 | 9/1980 | Terayama | 604/164 X |
| 4,512,768 | 4/1985 | Rangaswamy | 604/191 |
| 4,668,226 | 5/1987 | Omata et al. | 604/164 X |
| 4,791,937 | 12/1988 | Wang | 604/164 X |
| 4,808,156 | 2/1989 | Dean | 604/43 |

Primary Examiner—Dalton L. Truluck
Attorney, Agent, or Firm—Toren, McGeady & Associates

[57] ABSTRACT

The injection equipment for an endoscope comprises a guide tube (5) to be inserted into the instrument channel of the endoscope, in which two flexible tubes (7, 9) can be slid to supply the differing viscous fluid constituents in a two constituent fabric glue. At the distal end of the flexible tubes (7, 9) a twin tubular needle (15) is fitted, with its needle tubes (11, 13) opening out separately at the distal end. In this way the two constituents only mix inside the fabric. The flexible tubes (7, 9) also have a differing internal diameter like the two needle tubes (11, 13), whereby the more viscous constituents are fed via the larger diameter flexible tube (7), to which the larger diameter needle tube (11) is also connected. Handling is thereby facilitated and there is better compliance with the correct mixture ratio for both constituents.

5 Claims, 1 Drawing Sheet

INJECTION EQUIPMENT WITH A TWIN TUBULAR NEEDLE FOR AN ENDOSCOPE

The invention relates to injection equipment for an endoscope. Injection equipment which can be used in an endoscope is known from DE-A-35 36 779. Such injection equipment as a holding device which can be secured to the control unit of the endoscope, onto which a flexible guide tube, open at its distal end, i.e. the one located away from the operator, is fastened with its proximal end, i.e. the one facing the operator, extending the guide channel of the holding device. In the guide tube housed in the instrument channel of the endoscope a flexible feed tube can be moved with an injection needle secured at its distal end, which can be pushed out through the open end of the guide tube. The injection fluid is supplied to the feed tube from a syringe via the guide channel of the holding device.

Using the known injection equipment no substances consisting of several constituents, which must only be mixed just before injection, can be injected. In particular no two constituent fabric glues, such as two constituent fibrin glues for example, can be injected via the instrument channel of the endoscope. Injection equipment for an endoscope, with which one can inject two constituent substances especially two constituent glues, is known from the German registered patent 87 00 434. This injection equipment has an injection needle unit which consists of at least two needle tubes located next to one another parallel to the axis at least in the area of their distal ends and firmly connected together in at least a section of this area. The distal ends of the needle tubes open out next to one another and are preferably bevelled to recessed points, while the proximal ends of each of the needle tubes are connected to one of two flexible pipes located next to one another in the guide tube, supplying the injection fluids.

With this injection equipment a mixer head in the area of the tubular needles is dispensed with, since it is recognized that the pressure at which the injection fluids emerge from both needle tubes is sufficient to open out a chamber in the area of the tip of the tubular needle inserted in the fabric, in which both constituents can be adequately mixed.

Two constituent substances, for example two constituent fabric glues must be mixed in a pre-determined volumetric ratio. The syringes fixed in the area of the control unit, from which both constituents are supplied, are therefore in many cases connected into one unit to facilitate handling and the ratio of the piston areas of both syringes are dimensioned according to the mixing ratio, so that with the same piston strokes of both syringes both constituents are delivered in the correct mixture ratio. The pistons of both syringes can therefore also be connected to one another and can be operated together. Both constituents of the two constituent substance generally have very varying viscosity. While one constituent has a consistency similar to that of water, in many cases the other constituent has a viscosity comparable to that of honey. In practice it has been shown that due to the comparably small internal diameter of both flexible pipes, which is generally around a few tenths of a millimeter, a comparatively high peak pressure must be used, which makes the dosage more difficult, especially since generally only volumes of magnitude of a drop are injected. It has moreover been shown, that despite volumes being supplied in the correct mixture ratio, the mixture ratio of the constituents is not always correctly adhered to at the needle tube outlet.

The function of the invention is to produce injection equipment, which is easier to operate than hitherto and which guarantees the correct mixture ratio of the constituents in the two constituent substances to be injected in the area of the tubular needle outlets.

Within the scope of the invention both of the flexible pipes and both of the needle tubes have varying internal diameters, with the needle tube with the larger diameter also being connected to the flexible pipe with the larger diameter. The more viscous constituents of both of the constituents in the two constituent system which are to be mixed are fed via the larger diameter flexible pipe. The larger diameter needle tube reduces the throttle effect for the more viscous constituents, so that as a whole the pressure in the flexible tube is reduced. This reduces the danger, that both flexible tubes inflate differently due to varying internal pressures and the mixture ratio is distorted as a result on the outlet side of the needle tubes. Moreover the force required to operate the injection pistons is reduced, facilitating handling. The tips of the needle tubes can be bevelled to a common or to two separate tips in the way described in the German registered patent 87 00 434. In particular, in applications where perforations must be avoided, the terminating tubular needles can also be butt-ended.

As far as the flexible tubes are concerned, they can be tubes which are separate from one another. It is however expedient for the flexible tubes to be joined together as an extrusion moulded integral unit. It goes without saying that in addition to both the flexible tubes connected to the needle tubes further flexible tubes can be provided, down with gases, such as air for example, or else rinsing fluids and so on can be carried in the area of the needle tubes.

Figure 2:
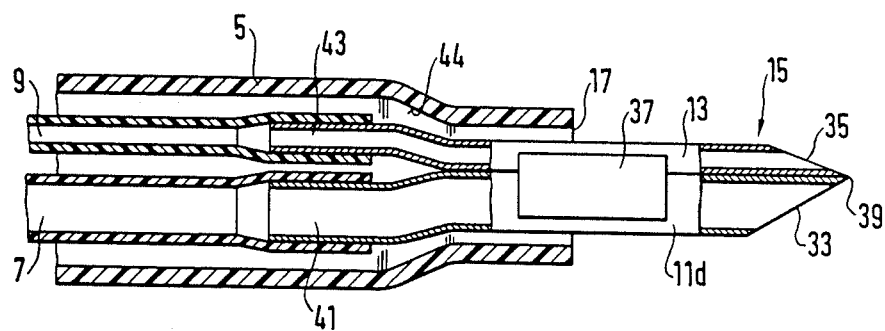
Figure 3:
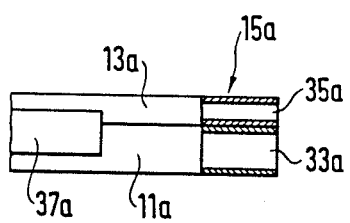
Figure 4:
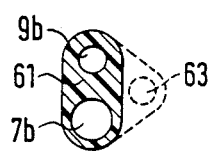

Examples of the design of this invention are explained in further detail below by means of a drawing. This shows:

FIG. 1 a diagram of injection equipment for an endoscope suitable for injecting two-constituent substances;

FIG. 2 a sectioned view through the distal end of the injection equipment;

FIG. 3 a version of a twin tubular needle which can be used with the injection equipment according to FIG. 1 and FIG. 4 a sectioned view through a version of a flexible tube arrangement with the injection equipment from FIG. 1.

The injection equipment shown in FIG. 1 makes it possible to inject a substance consisting of two liquid constituents via a flexible instrument channel of an endoscope or similar equipment which is not described in further detail, for example a two constituent fabric glue, whereby the two fluid constituents are only mixed together right at the injection point. Endoscopes, on which the injection equipment can be used, are known and will not be described any further. The two constituent fabric glues which are to be injected are also known.

The injection equipment comprises a tube shaped holder 1, which is secured for use on the control unit of the endoscope. The holder 1 has a tubular shape and forms a guide channel 3 extending over its whole length. At the distal end of the guide channel 3 i.e. the one away from the operator, a flexible guide tube 5 is connected, which is housed in the endoscope instrument channel when in use. In the guide tube 5 two flexible pipes 7, 9 are located next to one another, with their distal ends terminating in needle tubes 11, 13 joined into one unit of a twin tubular needle 15. The twin tubular needle together with the flexible pipes 7, 9 can be moved longitudinally in the guide tube 5, in order to be able to draw the twin hollow needle 15, which can be pushed out of the distal opening 17 of the guide tube 5, completely into the guide tube 5. At the proximal end i.e. the one adjacent to the operator, the flexible pipes 7, 9 are each connected to rigid tubes 19, 21 made of metal for example. The tubes 19, 21 are fixed in a jacket tube, for example by soldering. The jacket tube 23 can be slid into the guide channel 3 and can be locked with a fixing screw 25. By moving the jacket tube 23 relative to the holder 1 the twin tubular needle 15 can be pushed out of or drawn into the guide tube 5 and locked in each case.

At the proximal end of the tubes 19, 21 connecting units 27, 29, for example 'Luer-lock' connections are attached, to which a feed device 31, which can be detached, can be connected for the liquid constituents to be injected, for example a twin syringe or similar. The liquid constituents contained in the twin syringe, especially a two constituent fabric glue with a fibrin base for example, are fed to the needle tubes via the tubes 19, 21 and the flexible pipes 7, 9, and emerge separately from their distal outlets 33, 35 and mix together outside the needle tubes 11, 13. In the case of the twin tubular needle 15 inserted in the fabric to be treated both constituents mix within the fabric in a hollow opened out in the fabric or in the vicinity of the twin needle 15 due to the pressure of the fluid.

FIG. 2 shows details of the twin tubular needle 15, whose needle tubes 11, 13 are located in a parallel axis to one another at least in the distal section which can be pushed out of the guide tube 5 and are rigidly connected together in a section of this area by material accumulations 37. The material accumulations 37 provided either side of the needle tubes 11, 13 completely fill in the fillet area between the two tubes, with them not protruding beyond the diameter of the needle tubes 11, 13, so that they do not prevent the insertion of the twin tubular needle 15 in the fabric. The needle tubes can be glued, soldered or else welded together.

The distal ends of the needle tubes 11, 13 are bevelled away from one another, relative to a surface plane running between the two needle tubes 11, 13, so that a common insertion tip 39 is created located in the surface plane and both outlets 33, 35 are directed away from each other. In this way the fluid constituents emerging from the outlets 33, 35 cannot mix together on the direct path, which at least renders the formation of age-hardened plugs on the outlets 33, 35 more difficult. The material accumulations 37 end at a distance from the outlets 33, 35, in order to facilitate the insertion of the twin tubular needle 15 and the formation of the mixing cavity in the fabric.

The needle tubes 11, 13 are offset at their proximal ends 41, 43, so that they run away from one another and form push-on connections for the distal ends of the flexible tubes 7, 9. In order to make it more difficult to pull off the flexible tubes 7, 9, the ends 41, 43 can be fluted or fitted with a screw thread. The offset ends 41, 43 of the needle tubes 11, 13 form an enlargement, which can butt against a constriction 44 at the distal end of the guide tube 5 and restricts the discharge depth of the twin tubular needle 15, facilitating handling.

The internal diameter of the flexible tube 7 is larger than the internal diameter of the flexible tube 9. Equally the internal diameter of the needle tube 11 connected to the flexible tube 7 is greater than the internal diameter of the needle tube 13 connected to the flexible tube 9. In this way the constituents in a two constituent system can be supplied via the flexible tubes 7, 9 with a mutually adjusted internal pressure, if the more viscous of the two constituents or else in the case of systems with constituents to be mixed in varying volumetric ratios the constituents to be mixed in the larger volume percent are supplied via the larger diameter flexible tube 7.

As indicated in FIG. 1, the feed device 31 consists of two syringes 45, 47 joined to the connecting units 27, 28, whose pistons 49, 51 are dimensioned in such a way that the ratio of their surfaces is identical to the mixing ratio of both constituents in the two constituent system. Both pistons 49, 51 can therefore be connected together for operation, as outlined by 53.

FIG. 3 shows a version of a twin tubular needle 15a, which can be used instead of the twin tubular needle 15 of FIG. 1. The twin tubular needle 15a, which has needle tubes 11a and 13a located next to one another and rigidly connected together yet again by material accumulations 37a similar to the twin tubular needle 15a, are cut off in a common plane perpendicular to the axis of the tube and form flush outlets 33a and 35a. The twin tubular needle 15a can be used to particular advantage, when there is a fear of unwanted perforations.

Both flexible tubes 7, 9 of the injection equipment shown in FIG. 1 are designed as separate tubes. FIG. 4 shows a version, in which both of the flexible pipes 7b and 9b to be connected to a twin tubular needle are produced by the extrusion moulding method and are connected rigidly together via a cross bridge 61 basically over their whole length. The tube created in this way can contain at least one further channel 63 besides the channels 7b and 9b, as it emerges from opening 17. The distal end of the channel 63 can however also be extended beyond the distal ends of the channels 7b, 9b, so that when the twin tubular needle is pushed out it emerges with it through the opening 17. It goes without saying, that such an additional channel can also be produced by means of a separate additional flexible tube similar to the flexible tubes 7, 9. At the proximal end of the channel 63 or of the additional flexible tube a connecting unit for connecting a source of gas or liquid comes out of the jacket tube 23.

The flexible pipes 7b, 9b can also have other cross sectional shapes than those shown. A profile with a circular external contour is particularly suitable, in which case the larger diameter flexible 7b has a semi-circular shaped internal cross section, whilst the flexible tube 9b has a circular cross section and is located in the remaining semi-circular sector of the profile. The channel 63 can also be located in the remaining semi-circular sector.

I claim:

1. Injection equipment for an endoscope for simultaneous injection of two liquid components contained in a twin syringe, comprising: a holding device (1) with a guide channel (3); a guide tube (5) open at its distal end and with its proximal end extending the guide channel (3) fixed to the holding device (1); a flexible feed tube arrangement (7, 9) which is longitudinally displaceable in the guide tube (5) and includes two flexible feed tubes (7, 9) located next to one another in the guide tube (5), a first (7) of the flexible tubes having a larger inside diameter than the second (9) of the flexible tubes; an injection needle unit (15) secured at the distal end of the feed tubes (7, 9) which is slidable through the open end (17) of the guide tube (5) and has two needle tubes (11, 13) axially parallel to one another at least in the region of their distal ends and rigidly connected together in at least a section of this region, the distal ends (33, 35) of the needle tubes being arranged so as to discharge next to one another and their proximal ends each being connected to one of the flexible pipes (7, 9) respectively, the needle tube (11) the needle tube (11) connected to the larger diameter flexible tube (7) having a larger internal diameter than the other needle tube (13); and terminal connecting means for detachably connecting the twin syringe (31) through the guide channel (3) with the proximal ends of the feed tubes (7, 9) so that one of the two liquid components having a larger volume share or a higher viscosity is fed to the first feed tube (7), and the other of the liquid components is fed to the second fed tube (9).

2. Injection equipment according to claim 1, wherein the flexible tubes (7e, 9e, 63) are integrally joined together in an extrusion moulded unit.

3. Injection equipment according to claim 1 wherein at least one further flexible tube (63) is fitted in the guide tube (5), with its distal end terminating in the area of the twin tubular needle (15) and its proximal end able to be coupled to a feed device for liquids or gases.

4. Injection equipment according to claim 1 wherein the distal ends of the needle tubes (11, 13) are bevelled to a joint tip (39) by the formation of outlets (33, 35) directed away from one another.

5. Injection equipment according to claim 1 wherein both needle tubes are butt ended into a common surface plane.

* * * * *